United States Patent [19]

Freidinger et al.

[11] 4,235,886

[45] Nov. 25, 1980

[54] CYCLIC HEXAPEPTIDE SOMATOSTATIN ANALOGS

[75] Inventors: Roger M. Freidinger, Hatfield; Daniel F. Veber, Ambler, both of Pa.

[73] Assignee: Merck & Co., Inc., Rahway, N.J.

[21] Appl. No.: 89,827

[22] Filed: Oct. 31, 1979

[51] Int. Cl.³ ..................... A61K 37/00; C07C 103/52
[52] U.S. Cl. ............................... 424/177; 260/112.5 S
[58] Field of Search .................. 260/112.5 S; 424/177

[56] References Cited

U.S. PATENT DOCUMENTS

| | | | |
|---|---|---|---|
| 4,140,767 | 2/1979 | Veber et al. | 260/112.5 S |
| 4,161,521 | 7/1979 | Veber et al. | 260/112.5 S |
| 4,162,248 | 7/1979 | Strachan et al. | 260/112.5 S |

OTHER PUBLICATIONS

DerWent Abstract 26448b/14; of European Patent 1295 Apr. 4, 1979.

Primary Examiner—Delbert R. Phillips
Attorney, Agent, or Firm—David L. Rose; Harry E. Westlake

[57] ABSTRACT

Somatostatin analogs are prepared wherein a cyclic hexapeptide contains a secondary amino acid which replaces seven of the ring amino acids of somatostatin. The cyclic hexapeptides are easier to synethesize, have a longer duration of activity, and many have a greater level of activity than somatostatin. The compounds have the properties of inhibiting the release of glucagon, growth hormone and insulin. Certain of the compounds also are capable of inhibiting the release of gastric acid secretions. The compounds are particularly useful in the treatment of acromegaly, diabetes, diabetic retinopathy and peptic ulcers. These cyclic hexapeptides are prepared by the solid phase method.

12 Claims, No Drawings

CYCLIC HEXAPEPTIDE SOMATOSTATIN ANALOGS

BACKGROUND OF THE INVENTION

Somatostatin is a tetradecapeptide incorporating a cyclic dodecapeptide, having the structure:

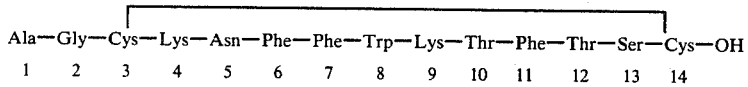

and has the properties of inhibiting the release of growth hormone, inhibiting the release of insulin and glucagon and reducing gastric secretions. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

SUMMARY OF THE INVENTION

The present invention provides for cyclic hexapeptides which are derivatives of somatostatin in which, inter alia, seven of the ring amino acids are replaced by a secondary amino acid, and both of the exocyclic amino acids are removed. Further substitution and reaction of the remaining amino acids is also described. The cyclic hexapeptides inhibit the release of glucagon, growth hormones and insulin, and inhibit the release of gastric acid secretions. Specifically the compounds may preferentially inhibit the release of growth hormones without effecting the level of gastric secretions or without effecting the level of gastric secretions, insulin and glucogon, or the compounds may inhibit the release of gastric acid secretions. Thus, the compounds have a more selective biological activity than somatostatin. The cyclic hexapeptide structure of the instant compounds also have a longer duration of activity than somatostatin. As such the instant cyclic hexapeptides are useful for the treatment of acromegaly, diabetes, diabetic retinopathy and peptic ulcers.

Thus, it is an object of the present invention to describe the cyclic hexapeptide somatostatin analogs. A further object is to describe procedures for the preparation of such cyclic hexapeptides. A still further object is to describe the use of such compounds in the treatment of acromegaly, diabetic retinopathy and peptic ulcers. Further objects will become apparent from reading the following description.

DESCRIPTION OF THE INVENTION

The compounds of the instant invention are best realized in the following structural formula:

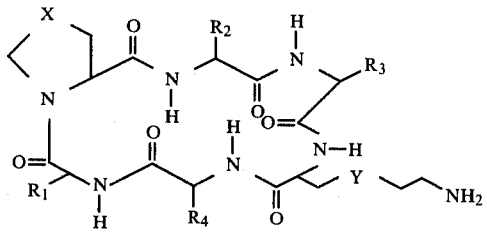

wherein X is $(CH_2)_n$ wherein n is 0, 1 or 2 or sulfur;

Y is $(CH_2)_m$ wherein m is 0, 1 or 2 or sulfur such that the sulfur may be in any position along the chain;

$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;

$R_3$ is 3-indolylmethyl or substituted 3-indolylmethyl wherein the substituent may be loweralkyl, loweralkoxy, or halogen; and $R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro.

The term "loweralkyl" when used in the instant application is intended to represent those alkyl groups either straight or branched chains, which have from 1-5 carbon atoms. Examples of such alkyl groups are methyl, ethyl, propyl, iso-propyl, butyl, sec-butyl, pentyl and the like.

The term "loweralkoxy" is intended to include those alkoxy groups of from 1-5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the instant compounds there are several assymetric centers which will lead to the existence of optical isomers for such compounds. In the instant invention, for each of the assymetric centers of the various amino acids which will make up the instant cyclic hexapeptides, both the D and L configurations are intended to be encompassed.

It will be appreciated by those skilled in the art that when $R_1$ and $R_2$ are benzyl, $R_3$ is indolylmethyl, Y is methylene, and $R_4$ is 1-hydroxyethyl, the 7,8,9,10 and 11 amino acids of somatostatin (-Phe-Trp-Lys-Thr-Phe-) are represented, and the secondary amino acid, represented by proline when X is methylene, has taken the place of the remainder of the somatostatin amino acids. Thus, using the above definitions of the substituent groups, the following representative cyclic hexapeptide analog of somatostatin is formed:

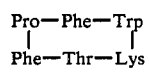

The preferred embodiments of the cyclic hexapeptides of this invention are realized in the foregoing structural formula wherein X and Y are $(CH_2)_n$ and n is 1;

$R_1$ and $R_2$ are as defined above;

$R_3$ is 3-indolylmethyl or substituted indolylmethyl wherein the substituent is methoxy of fluoro; and $R_4$ is methyl, ethyl, hydroxy methyl or hydroxy ethyl.

Further preferred embodiments are realized when X and Y are methylene;

$R_1$ and $R_2$ are as defined above;

$R_3$ is 3-indolylmethyl; and $R_4$ is hydroxy ethyl.

$R_1$ and $R_2$ are as defined above.

The preferred $R_1$ and $R_2$ groups are loweralkyl, benzyl or substituted benzyl where the substituent is loweralkyl, halogen, hydroxy, amino, nitro or alkoxy.

Included within these preferred compounds are:
Cyclo-(Pro-Tyr-D-Trp-Lys-Thr-Phe)
Cyclo-(Pro-Phe-D-Trp-Lys-Thr-Phe)
Cyclo-(Pro-Phe-L-Trp-Lys-Thr-Phe)
Cyclo-(Pro-Phe-D-Trp-Lys-Thr-p-Cl-Phe)
Cyclo-(Pro-Phe-D-5-F-Trp-Lys-Thr-Phe)
Cyclo-(Pro-Phe-L-5-F-Trp-Lys-Thr-Phe)
Cyclo-(Pro-Phe-D-Trp-Lys-Ser-Phe)

In the instant application several abbreviated designations are used for the amino acid components, certain preferred protecting groups, reagents and solvents. The meanings of such abbreviated designations are given in Table I.

TABLE I

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D- or L-aminosuberic acid |
| Cys | L-cysteine |

| Abbreviated Designation | Protecting Groups |
|---|---|
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |
| 2-Cl-CBZ | 2-chlorobenzyloxycarbonyl |
| Acm | acetamidomethyl |

| Abbreviated Designation | Activating Groups |
|---|---|
| ONp | p-nitrophenyl ester |
| HSE | N-hydroxysuccinimide ester |
| HBT | 1-hydroxybenzotriazole |

| Abreviated | Condensing |
|---|---|

TABLE I-continued

| Designation | Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |

| Abbreviated Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel cyclic hexapeptide somatostatin analogs are prepared by cyclizing corresponding linear peptides. The linear peptides are prepared by using the solid phase sequential synthesis technique. Accordingly, the process for preparing the cyclic hexapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain blocking groups.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example D-Trp can react with t-butyl carbonium ions which are formed when BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1-2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups. After the linear peptide is cyclized, the protective groups, such as 2-Cl-CBZ and Bzl, are removed by treatment with HF.

After the linear peptide has been formed on the solid phase resin, it may be removed from the resin by a variety of methods which are well known in the art. For examples, the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of hydrazine.

As reference Table II will show, one preferred overall procedure for preparing the desired cyclic peptides of the present invention involves the stepwise synthesis of the linear peptide on a solid phase resin. More specifically, in the process for preparing:

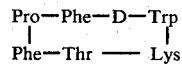

the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence:

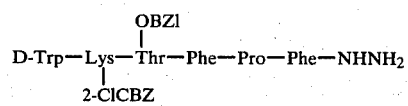

is treated with isoamyl nitrite in acid pH to form the corresponding azide. The azide solution is diluted with solvent and neutralized with an organic base. The linear peptide cyclizes to form:

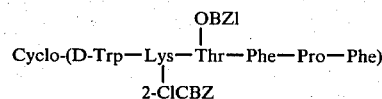

During the cyclization the "pH" is checked and maintained at neutral by the addition of organic base. The "pH" in organic solvent is determined by the application of an aliquot of the solution to moistened narrow range pH paper.

After the linear peptide is cyclized, the protective groups, 2-Cl-CBZ and OBZl, are removed by treatment with HF in the presence of anisole. The crude cyclic peptide obtained is purified chromatographically, preferably with column chromatography on silica gel. The elution solvent is generally an organic solvent to mixtures thereof which is selected by analyzing aliquots of the material using thin layer chromatography.

TABLE II

The reaction scheme for the preparation of one of the cyclic hexapeptides of this invention is outlined in the following series of reactions:
Reaction scheme for preparing:

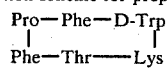

TABLE II-continued

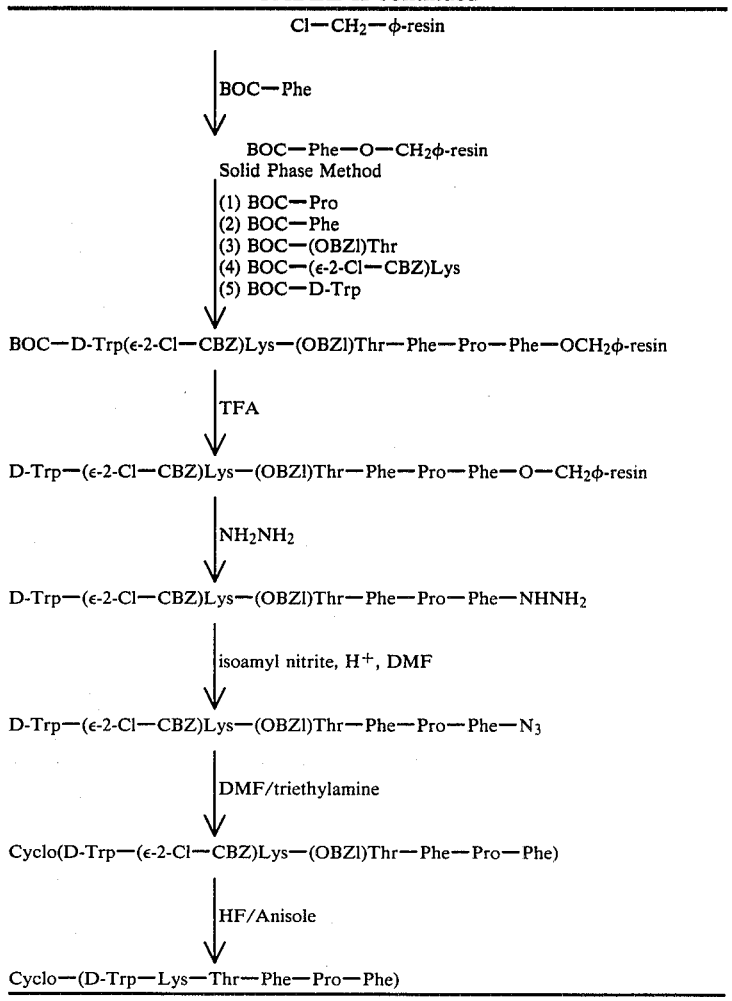

The following Examples are given to illustrate the methods used to carry out the present invention. It is to be understood that these Examples are given for purposes of illustration and not limitation.

EXAMPLE 1

Preparation of D-Trp-(ε-2-Cl-CBZ)Lys-(OBZl)Thr-Phe-Pro-Phe-OCH₂φ-resin

Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperatures for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3×2000 ml. of tetrahydrofuran
4×5170 ml. of ethanol
1×5170 ml. of acetic acid
3×5170 ml. of water
3×5170 ml. of methanol
3×5170 ml. of chloroform The BOC-Phe-O-CH$_2$-φ-resin was dried in vacuo at 25° C. for 16 hours, giving 1203 g. of BOC-Phe-O-CH$_2$-φ-resin containing 1.2 mmole of phenylalanine/g. of resin.

BOC-Phe-O-CH$_2$φ-resin (2.13 g.; 2.0 mmole) was carried through the procedures in Tables III and IV using 2 deblockings (2 minutes and 25 minutes) with 25% TFA in methylene chloride and 2.5 equivalents of BOC-amino acid in the required sequence until the desired BOC-hexapeptide-O-CH$_2$φ-resin was obtained.

DCCI was used as the sole coupling agent in every step.

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl in the ε-amino group of Lys with 2-Cl-CBZ.

When the desired BOC-hexapeptide-O-CH$_2$-φ-resin was obtained, the N-terminal BOC group was removed by the terminal deblocking procedure set forth in Table V.

TABLE III

| Solvent or reagent (number of treatments or washes) | CHCl$_3$ (2) | 25% TFA in CH$_2$Cl$_2$ (2) | CHCl$_3$ (3) | NEt$_3$-CH$_2$Cl$_2$ (1:9) (2) | CHCl$_3$ (3) CH$_2$Cl$_2$ (3) | BOC AA in CH$_2$Cl$_2$ DMF or a mixture of both | 0.5M D = Cl in CH$_2$Cl$_2$ | DMF (1) MeOH (1) DMF (1) MeOH (1) CHCl$_3$ (2) |
|---|---|---|---|---|---|---|---|---|
| Vol. in ml. | 40 | 20 | 40 | 40 | 40 | 25 | 10 | 40 |
| Time in min. | 5 | 2 and 25 | 2 | 5 and 5 | 2 | 5 | 5 coupling 30 | 2 |

TABLE IV

| Protected Amino Acid | Solvent Ml. |
|---|---|
| BOC-Pro (1.08 g.) Recouple | 25 ml. CH$_2$Cl$_2$ |
| BOC-Phe (1.32 g.) Recouple | 25 ml. CH$_2$Cl$_2$ |
| BOC (OBZ)Thr (1.55 g.) Recouple | 25 ml. CH$_2$Cl$_2$ |
| BOC-(2-Cl-CBZ)Lys (2.24 g.) Recouple | 25 ml. CH$_2$Cl$_2$ |
| BOC-D-Trp (1.52 g.) Recouple | 20 ml. CH$_2$Cl$_2$, 5 ml. DMF |

TABLE V
TERMINAL DEBLOCKING PROGRAM

| Solvent or reagent (number of treatments CH$_2$Cl$_2$ (2) or washes) | CHCl$_3$ (1) | 25% TFA in CH$_2$Cl$_2$ + 1% Ethanedithiol (2) | CHCl$_3$ (3) | MeOH (2) CH$_2$Cl$_2$ (1) MeOH (2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked hexapeptide-OCH$_2$φ-resin is dried overnight and weighs 3.7 g.

EXAMPLE 2

Preparation of D-Trp-(ε-2-Cl-CBZ)Lys-(OBZl)Thr-Phe-Pro-Phe-NHNH$_2$

The resin from Example 1 is combined with 30 ml. of a 2:1 mixture of dimethylacetamide and hydrazine and stirred at room temperature for 1 hour. The insoluble resin is removed by filtration and the solution is evaporated to remove the dimethylacetamide. The residue is placed under high vacuum overnight to remove all volatile materials. A foam resulted from dissolving the residue in methanol, filtering and evaporating to dryness, weighing 1.84 g.

EXAMPLE 3

Preparation of D-Trp-(ε2-Cl-CBZ)Lys-(OBZl)Thr-Phe-Pro-Phe-N$_3$

The foam from Example 2 is combined with 15 ml. of degassed dimethylformamide under a blanket of nitrogen and cooled to −10° C., and 5 equivalents of 5.8 M. hydrogen chloride in tetrahydrofuran (1.7 ml.) is added. The solution is cooled to −25° C. and 5 ml. of a 1:19 mixture is isoamyl nitrite in dimethylformamide is added. The completion of the reaction is followed by thin layer chromatography and the disappearance of the hydrazide starting material.

EXAMPLE 4

Preparation of Cyclo(D-Trp-(ε-2-Cl-CBZ)Lys-(O-BZl)Thr-Phe-Pro-Phe)

The azide compound of Example 3 is added to 600 ml. of degassed dimethylformamide, precooled to −25° C., the pH adjusted to 8, and the reaction mixture placed in the freezer overnight. The pH is readjusted to 8 if necessary after about 14 hours and the mixture stored for 16 hours at −20° C. and 16 hours at 5° C. Thin layer chromatography indicates that the reaction is completed. The mixture is concentrated to dryness dissolved in 150 ml. of a 3:1 dimethylformamide/water mixture and treated with a mixed bed anion-cation exchange resin for 2 hours. The mixture is filtered and concentrated to dryness in vacuo, and the residue is dissolved in methanol, filtered and evaporated to dryness affording a foam.

EXAMPLE 5

Preparation of Cyclo(D-Trp-Lys-Thr-Phe-Pro-Phe)

2.13 G. (2 mmoles) of the protected cyclic hexapeptide of Example 4 is combined with a teflon lined chamber with 2 ml. of anisole. The chamber is then evacuated and filled with liquid hydrogen fluoride at a temperature of the dry ice/acetone bath. The temperature is raised to 0° C. and stirring continued for 1 hour. The hydrogen fluoride is allowed to evaporate and the residue placed in vacuo until a slurry is formed. The slurry is treated with ethyl acetate and filtered affording 1.19 g. of a fine powder. 300 Mg. of this powder is placed on a 1000μ silica gel preparative layer chromatography plate and eluted with a 70:30:5 mixture of chloroform, methanol and concentrated aqueous ammonia, affording 200 mg. of product. The remaining crude product is placed on a silica gel column, and eluted with the same solvent. The presence of the product in the eluent is determined by thin layer chromatographic analysis and, after freeze drying, affords about 510 mg. of product.

Following the above procedure, and by modifying only the selection and order of amino acids in the process of Example 1, there are prepared other cyclic hexapeptides of this invention.

The instant cyclic hexapeptide analogs of somatostatin are tested and compared with the effects of somatostatin in an in vitro test for the inhibition of growth hormone. The test is described as follows:

"Rat pituitaries were isolated according to the procedures of Vale and Grant "In vitro Pituitary Hormone Secretion Assay for Hypophysiotropic Substances" in Methods in Enzymology. Vol. XXXVII, eds. O'Malley, B. W. and Hardman, J. G. (Academic Press, Inc., New York) pp. 5–93 (1975).

After 4 days in culture, the cells were washed and incubated for 4 hours in Dulbecco-modified Eagle's medium in the presence or absence of graded doses of each analog or somatostatin. The medium was then collected for subsequent growth hormone determination by a double antibody radioimmunoassay for rat growth hormone."

The test results for some of the compounds of this invention are recorded below with the results for somatostatin listed first and given the arbitrary value of 1. The results for the instant compounds are given as multiples or fractions of the effect of somatostatin. The numbers in parentheses are the fiducial limits for the number preceding. The first of the instant compounds listed is the compound prepared in Example 1-5. The compound is written slightly different, however, to conform to the order of the amino acids found in somatostatin.

| Activity of Cyclichexapeptide Analogs of Somatostatin. | |
|---|---|
| Compound | Growth Hormone Release Inhibition In Vitro |
| Somatostatin | 1 |
| Cyclo(Pro-Phe-D-Trp-Lys-Thr-Phe) | 1.71 (1.31–2.32) |
| Cyclo(Pro-Phe-L-Trp-Lys-Thr-Phe) | 1.59 (1.33–1.92) |
| Cyclo(Pro-Phe-D-5F-Trp-Lys-Thr-Phe) | 2.4 (2.1–2.8) |
| Cyclo(Pro-Phe-L-5F-Trp-Lys-Thr-Phe) | 2.5 (1.9–3.2) |
| Cyclo (Pro-Phe-L-5-OCH3-Trp-Lys-Thr-Phe) | 0.17 (0.12–0.25) |
| Cyclo-Phe-D-Trp-Orn-Thr-Phe) | 0.16(0.15–0.17) |
| Cyclo(Pro-Phe-D-Trp-Lys-ser-Phe) | 1.4 (1.1–1.7) |
| Cyclo(Pro-Phe-D-Trp-Lys-α-ABU-Phe) | 0.82 (0.57–1.18) |
| Cyclo(Pro-Phe-D-Trp-Lys-Thr-Leu) | 0.16 (0.07–0.33) |
| Cyclo(Pro-Phe-D-Trp-Lys-Thr-p-Cl-Phe) | 0.86 (0.75–1.0) |
| Cyclo(Pro-p-Cl-Phe-D-Trp-Lys-Thr-Phe) | 1.14 (0.98–1.34) |
| Cyclo(Pro-Leu-D-Trp-Lys-Thr-Phe) | 0.29 (0.13–0.57) |
| Cyclo(Pro-Ala-d-Trp-Lys-Thr-Phe) | 0.19 (0.1–0.38) |
| Cyclo)Pro-Tyr-D-Trp-Lys-Thr-Phe) | 14.3 (8.3–33.0) |

The effects of the instant cyclichexapeptide analogs of somatostatin are determined by the following procedure.

Compounds were tested for their ability to inhibit pentagastrin evoked gastric secretion in the chronic fistula dog. Female beagle dogs with a chronic gastric fistula were given pentagastrin (2.5 μg./kg./hour, i.v. from −60 to 120 min.) and gastric outputs were collected via the fistula cannula. Samples were analyzed at 30 minute intervals for volume (ml.) and titratable acid (mEq/L) (Titration to pH 7 with 0.01 N NaOH); total acid output (mEq) was calculated as the production of output volume and acid concentration. Test compounds were infused at a constant rate from 0 to 60 minutes. Data have been expressed as percent change of total acid output relative to a placebo trial in the same animals.

| Effects of Cyclichexapeptide Analogs of Somatostatin on Gastric Secretion (Dose 0.8 μg/ml./min./ - infusion 0-60 min.) | | | | | | | | |
|---|---|---|---|---|---|---|---|---|
| | Gastric Secretion % Inhibition | | | | | | | |
| Compound | Vol. | | | | Acid Concentration | | | |
| | 0–30 | 30–60 | 60–90 | 90–120 | 0–30 | 30–60 | 60–90 | 90–120 |
| Somatostatin | 85 | 97 | 81 | 37 | 16 | 77 | 61 | 14 |
| Cyclo(Pro-Phe-D-Trp-Lys-Thr-Phe) | 88 | 98 | 95 | 86 | 18 | 47 | 54 | 68 |
| Cyclo(Pro-Phe-D-Trp-Lys-Thr-p-Cl-Phe) | 88 | 88 | 85 | 44 | 52 | 82 | 94 | 38 |
| Cyclo(Pro-p-Cl-Phe-D-Trp-Lys-Thr-Phe) | 79 | 94 | 51 | 25 | 30 | 53 | 24 | 12 |
| Cyclo(Pro-Tyr-D-Trp-Lys-Thr-Phe) | 67 | 87 | 87 | 64 | 30 | 49 | 52 | 27 |

What is claimed is:
1. A compound having the formula:

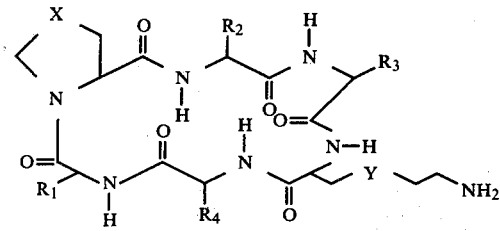

wherein X is $(CH_2)_n$ wherein n is 0, 1 or 2 or sulfur;

Y is $(CH_2)_m$ wherein m is 0, 1 or 2 or sulfur such that the sulfur may be in any position along the chain;

$R_1$ and $R_2$ are independently lower alkyl, benzyl, substituted benzyl wherein the substituent may be one or two of loweralkyl, halogen, hydroxy, amino, nitro or loweralkoxy; and loweralkyl substituted with a 5- or 6-membered heterocyclic ring;

$R_3$ is 3-indolylmethyl or substituted 3-indolylmethyl wherein the substituent may be loweralkyl, loweralkoxy or halogen; and $R_4$ is loweralkyl, hydroxyloweralkyl, benzyl, carboxyloweralkyl, aminoloweralkyl or substituted hydroxy benzyl wherein the substituent may be loweralkyl, loweralkoxy, hydroxy, halogen, amino or nitro.

2. A compound of claim 1 wherein X and Y are $(CH_2)_n$ and n is 1;
$R_1$ and $R_2$ are as defined in claim 1;
$R_3$ is 3-indolylmethyl or substituted indolylmethyl wherein the substituent is methoxy or fluoro; and
$R_4$ is methyl, ethyl, hydroxymethyl or hydroxyethyl.

3. A compound of claim 2 wherein:
X and Y are methylene;
$R_1$ and $R_2$ are as defined in claim 1;
$R_3$ is 3-indolylmethyl; and
$R_4$ is hydroxyethyl.

4. The compound of claim 2 which is cyclo (Pro-Tyr-D-Trp-Lys-Thr-Phe).

5. The compound of claim 2 which is cyclo (Pro-Phe-D-Trp-Lys-Thr-Phe).

6. The compound of claim 2 which is cyclo (Pro-Phe-L-Trp-Lys-Thr-Phe).

7. The compound of claim 2 which is cyclo (Pro-Phe-D-5F-Trp-Lys-Thr-Phe).

8. The compound of claim 2 which is cyclo (Pro-Phe-L-5F-Trp-Lys-Thr-Phe).

9. The compound of claim 2 which is cyclo (Pro-Phe-D-Trp-Lys-Ser-Phe).

10. The compound of claim 2 which is cyclo (Pro-Phe-D-Trp-Lys-Thr-p-Cl-Phe).

11. A method for inhibiting the release of growth hormone which comprises administering to an animal an effective amount of a cyclic hexapeptide of claim 1.

12. A pharmaceutical composition for inhibiting the release of growth hormone comprising a therapeutically effective amount of the cyclic hexapeptide of claim 1 or the non-toxic acid addition salts thereof in a pharmaceutically acceptable liquid or solid carrier.

* * * * *